US007655255B2

(12) United States Patent
Liu et al.

(10) Patent No.: US 7,655,255 B2
(45) Date of Patent: *Feb. 2, 2010

(54) TOPICAL COMPOSITION FOR TRANSDERMAL ADMINISTRATION

(75) Inventors: BuSang Liu, Sanchong (TW); TongHo Lin, Taipei (TW)

(73) Assignee: HenKan Pharmaceutical Co., Ltd., Taipei (TW)

( * ) Notice: Subject to any disclaimer, the term of this patent is extended or adjusted under 35 U.S.C. 154(b) by 422 days.

This patent is subject to a terminal disclaimer.

(21) Appl. No.: 10/811,420

(22) Filed: Mar. 26, 2004

(65) Prior Publication Data

US 2004/0228908 A1 Nov. 18, 2004

(30) Foreign Application Priority Data

May 16, 2003 (CN) .................. 03 1 36028
May 16, 2003 (WO) ..................... PCT/CN03/00358

(51) Int. Cl.
*A61K 9/70* (2006.01)
*A61K 71/08* (2006.01)
*A61K 27/00* (2006.01)

(52) U.S. Cl. ...................... 424/449; 514/168; 424/401; 424/357; 424/180

(58) Field of Classification Search ................. 424/464, 424/59, 449, 401, 357, 180; 514/474, 168
See application file for complete search history.

(56) References Cited

U.S. PATENT DOCUMENTS

| 5,438,073 | A |   | 8/1995  | Saurat et al. |
| 5,602,183 | A |   | 2/1997  | Martin et al. |
| 5,804,594 | A |   | 9/1998  | Murad |
| 5,962,517 | A | * | 10/1999 | Murad ........................ 514/474 |
| 6,217,852 | B1| * | 4/2001  | Gildenberg et al. ........... 424/59 |
| 6,630,163 | B1| * | 10/2003 | Murad ........................ 424/464 |

OTHER PUBLICATIONS

Chinese PCT Search Report for Application No. PCT/CN 03/00358, dated May 16, 2003 (6 pages).
English translation of Chinese PCT Search Report for Application No. PCT/CN 03/00358, dated May 16, 2003 (4 pages).
Abstract of Chinese Patent No. CN-1236634 (Li Hua), Dec. 1, 1999 (cited in above Search Report, third citation) (2 pages).
Office Action issued Jul. 31, 2009, by the U.S. Patent and Trademark Office in related-U.S. Appl. No. 11/446,051 (16 pages).

* cited by examiner

*Primary Examiner*—Ardin Marschel
*Assistant Examiner*—Zohreh Vakili
(74) *Attorney, Agent, or Firm*—Osha • Liang LLP

(57) ABSTRACT

The present invention relates to a topical composition for transdermal administration, wherein main components of the composition comprises vitamin C, vitamin B complex, carotene, and vitamin E, and may further comprise a fragrance, a thickening agent and a surfactant. The pharmaceutical composition is for topical application and is useful in skin-care and for the treatment of acne, comedo and zit. The composition also has an antioxidant property.

9 Claims, 1 Drawing Sheet

TOPICAL COMPOSITION FOR TRANSDERMAL ADMINISTRATION

CROSS-REFERENCE TO RELATED APPLICATIONS

This claims priority from Chinese Patent Application Ser. No. 03136028.9 filed May 16, 2003 and PCT International Application Serial No. PCT/CN03/00358 filed May 16, 2003.

BACKGROUND OF THE INVENTION

1. Field of the Invention

The present invention relates to topical compositions for transdermal administration. More particularly, the present invention relates to pharmaceutical compositions for nourishing and improving skin and for treating acne, comedo and zit.

2. Description of the Prior Art

Human skin structure consists of epidermis, dermis, subcutaneous fatty tissue, sebaceous gland, sweat glands, and hairs. The thick layer under the epidermis is the dermis. The hairs are surrounded by hair follicles, which have associated sebaceous glands. The sebaceous glands can secrete sebum, which will permeate to the surface of the skin by the hairs and hair follicle, and then becomes fatty film. The fatty film will attach to the surface of the skin and protect the skin. Skin types may be classified according to the quantity of sebaceous glands as oily skin, dry skin, and mixed-type skin.

Acne is a chronic inflammation in the hair follicle and the sebaceous gland. Acne is also commonly known as comedo or zit. It is usually found on the forehead, around the nose wing, and on the cheeks. It can also be found on any part of the body with hair follicles, such as the back, thoracic part, and thigh. Depending on the symptoms, acne can be classified as acne-type, inflammatory and red swelling type, and cyst-type. When gonads of adolescents mature, androgenic hormone in the testes and ovaries increases Androgenic hormone stimulates the sebaceous glands. As a result, the sebaceous glands become hypertrophic and secrete abundant sebum, which accumulates around the sebaceous glands and hair follicles. The accumulated sebum may become infected by bacteria. Usually, acne with a white or black head is formed first; it subsequently becomes papule, pustule, node and cyst after bacterial infection. Finally, a zit is formed. When too much androgenic hormone is secreted, redness, tickle, heat, burning sensation, and skin peeling may occur around the T area of the face or the skin under the eyelids. This sometimes leads to seborrheic dermatitis, which is characterized by the appearance of visible microvessels.

To prevent these problems, topical preparations are needed to clean the skin, kill the bacteria, prevent water evaporation, and improve moisture retention. Examples of topical preparations for these purposes include a cream containing sodium chloride for mollifying and soothing the skin disclosed in U.S. Pat. No. 3,574,854, and a skin-care composition containing mineral salts disclosed in German patent publication No. DE 3,327,840. Furthermore, U.S. Pat. No. 3,859,436 disclosed a glucose mixture for soothing skin, and U.S. Pat. No. 3,777,597 disclosed a shaving aqueous solution comprising glucose.

Sodium Chloride, especially 0.9% sodium chloride solution, i.e., saline, is the main composition in maintaining the osmotic pressure of body fluids. A solution containing a higher concentration of sodium chloride cannot be absorbed by the skin. Instead, it will irritate the skin mucosa and results in dehydration. Thus, topical preparations containing sodium chloride may irritate skin or kill bacteria. However, sodium chloride can hardly prevent water evaporation from skin or improve moisture retention. Glucose may increase glycogen, ensure cellular functions, improve metabolism by functioning as a nutritional agent. In addition, it may function as a detoxification agent. However, these effects cannot be achieved by applying the topical preparations containing glucose to the skin. Instead, glucose must be administered orally, intravenously and intramuscularly to have these effects.

There have been many therapeutic agents and cosmetics for treating various skin conditions, such as Hydrocortisone for treating atopic dermatitis with titillate and erythema, sulconazole nitrate for treating mycotic infection in the skin, tretinoin for treating light-induced aging, and 5-fluorouracil for treating psoriasis and skin cancer. Therapeutic agents for use in treating dermatologic diseases usually include permeation enhancers, such as dimethyl sulfoxide (DMSO), dimethyl formamide, methyldecyl sulfoxide (U.S. Pat. No. 3,527,864), dimethyl acetamide (U.S. Pat. No. 3,472,931) and N-alkyl-2-pyrrolidone (U.S. Pat. No. 3,696,516). However, the above-described permeation enhancers have certain disadvantages. For example, dimethyl sulfoxide has some odor and body odor, can burn the skin and induce erythema on skin, can reduce the transparency of crystalline-skin, and can even cause tissue necrosis in the animals. (Martindale, The Extra Pharmacopoeia, pages 1461-1463, $27^{th}$ Ed., 1977). Dimethyl formamide and dimethyl acetamide can also burn the skin and induce erythema on skin.

Moreover, Trebosc et al.(U.S. Pat. No. 5,030,451) disclosed a cosmetics composition containing improved derivatives of caffeine as active ingredients. The formulation has excellent and long-acting "lipolytic" properties and has proven very effective in weight loss programs and in the treatment of cellulite. An anti-cellulite composition containing methylsilanol theophyllin acetate alginate and methylsilanol mannuronate is disclosed by Mausner in U.S. Pat. No. 5,215,759. In U.S. Pat. No. 5,051,449, Kligman disclosed a method of reducing cellulite by locally applying retinoid to skin. Kligman reported that the treated subjects have a thickened epidermis and an increased number of new blood vessels, with a moderate to noticeable degree of improvement in the pinching test.

Topical aminolevulinic acid-photodynamic therapy for the treatment of acne vulgaris is disclosed in U.S. patent application No. 20020099094 A1. U.S. patent application No. 2002006185 A1 disclosed a composition for treating acne comprising water and glycol, and U.S. patent application No. 20010056071 A1 disclosed a composition for treating acne comprising resveratrol (3,4',5-trihydroxy-trans-stilbene), melatonin, Vitamins D, E, and A.

In addition, Shapiro, S. S. and Saliou, C. described that vitamin A, vitamin D and their derivatives in combination with vitamin C, vitamin E, and coenzyme Q could improve skin conditions and cure acne (*Nutrition* 2001, Vol. 17(10), pages 839-844). Vitamin A acid (i.e., Tretinoin or Retinoids) is a derivative of Vitamin A, and its major function is to remove cutin because it can remove the cutin on the epiderm. In addition, it can alleviate occlusion of the pores, reduce wrinkles and improve blood circulation around the face, decrease scar of pigment, and prevent skin keratinization, promote refreshing and sloughing off of epithelium cells, prevent synthesis of keratin, and prevent the formation of blister on the face. However, most Vitamin A acid-containing products may make the skin sensitive to the light, and overuse of these products may cause side effects, such as dry, red swelling, itching and dermatitis, etc.

From the foregoing, although there are patents disclosing compositions for the therapy of acne, decomposing fat or treating various skin symptoms, all these compositions have some defects and may do harm to the skin. Accordingly, the present invention provides a Vitamin A acid-free topical composition for transdermal administration.

SUMMARY OF THE INVENTION

The objective of this invention is to provide a topical composition for transdermal administration, said composition is free of Vitamin A acid and may be used for skin-care, treating acne and zit, and has an anti-oxidation property.

The invention provides a topical composition for transdermal administration, which mainly comprises vitamin C 1~45% W/W, vitamin B complex 1~5% W/W, carotene 1~3% W/W, and vitamin E 2~90% W/W.

The invention provides a topical composition for transdermal administration, mainly comprising 4~15% W/W vitamin C, 1~3% W/W vitamin B complex, 1~2% W/W carotene, and 20~65% W/W vitamin E. The composition may further comprise 0.1~2% W/W fragrance, 1~5% W/W thickening agent, 1~8% W/W surfactants, and an appropriate amount of distilled water.

The above-described topical compositions are for application to local areas of the skin.

The present invention also provides a topical composition for transdermal administration, which is used for the manufacture of medications useful in the treatment of acne, comedo and zit. Said composition may also be used for nourishing skin and has an anti-oxidation property. The composition mainly comprise 1~45% W/W vitamin C, 1~5% W/W vitamin B complex, 1~3% W/W carotene, 2~90% W/W vitamin E, 0.1~2% W/W fragrance, 1~5% W/W thickening agent, 1~8% W/W surfactants, and an appropriate amount of distilled water.

The invention provides a topical composition for transdermal administration, which mainly comprises 1~45% W/W vitamin C, 1~5% W/W vitamin B complex, 1~3% W/W carotene, 2~90% W/W vitamin E, 0.1~2% W/W fragrance, 1~5% W/W thickening agent, 1~8% W/W surfactant and the remainder is distilled water; the sum of the content of the components is 100%.

The invention provides a topical composition for transdermal administration, useful in the treatment and prevention of acne, comedo and zit of the skin.

The present invention provides a composition for skin care. A composition of the invention can also be used to improve the acne, comedo and zit of the skin, and has an anti-oxidation property. As the composition is free of Vitamin A acid, it will not induce skin sensitivity to light and will improve skin conditions without causing skin dryness, red swelling, itching, and inflammation. There is no over dosage problem even with long term use.

With the following detailed description of examples and the associated drawings, the objectives, techniques, advantages, and utility of the present invention may be better appreciated.

DESCRIPTION OF THE PREFERRED EMBODIMENTS

Figure 1:
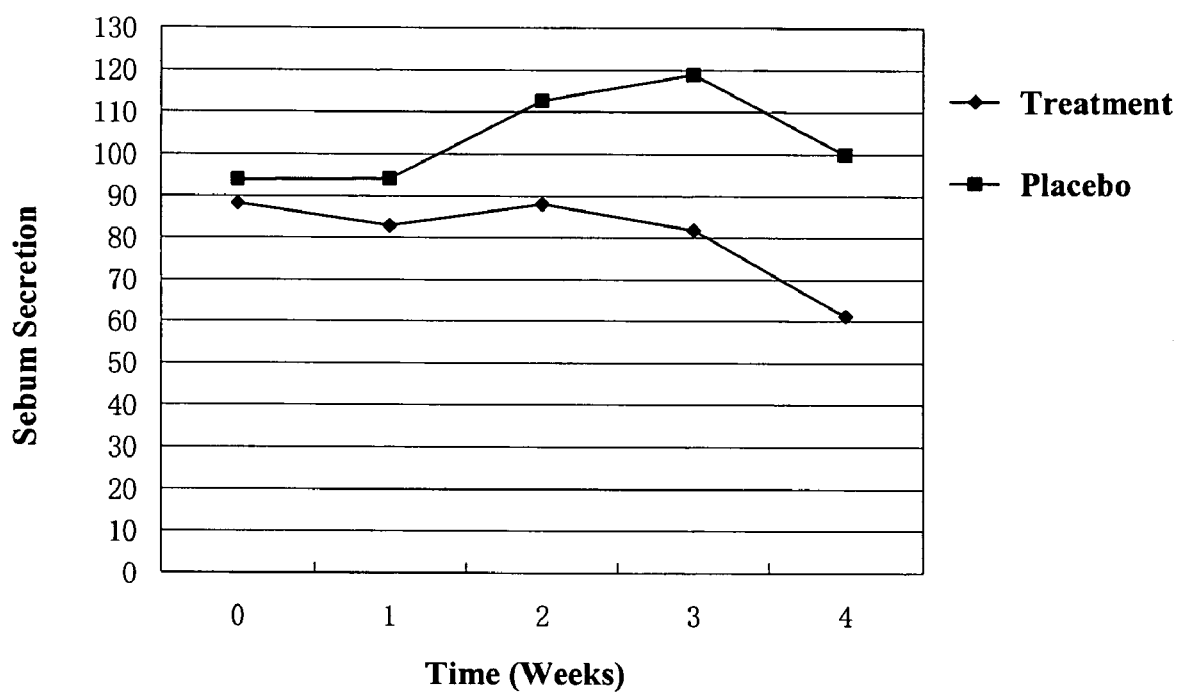
FIG. 1 shows the difference in sebum secretion by the skin before and after administrating a topical composition of the invention, wherein the abscissa is time (week) and the ordinate is the quantity of sebum ($\mu g/cm^2$) secreted by the skin.

This invention provides a topical composition for transdermal administration, which is free of Vitamin A acid and is used for skin care and for treating and improving the symptoms of acne, comedo and zit of the skin.

The topical composition according to one embodiment of the present invention mainly comprises vitamin C, vitamin B complex, carotene, vitamin E, a fragrance, a thickening agent, and surfactants. The main components of the composition are the essential Vitamins, but free of Vitamin A acid. Therefore, there is no problem with over-dosage even after long-term use.

The need of vitamins is very small in the body, but the functions of vitamins are vital. Vitamins cannot be synthesized by human and need to be taken in from outside sources. The major functions of vitamin C in the body are as follows: preventing the formation of peroxylipid, facilitating the formation of collagen, assisting various enzymes, retarding aging of cells, as well as improving blood circulation, and reducing melanin. Therefore, vitamin C is commonly believed to contribute to skin's regeneration, to prevent the generation of melanin and to enhance the immunity.

Vitamin B complex is a combination of various vitamins, such as vitamin $B_1$ (thiamin), vitamin $B_2$ (riboflavin), Niacin, vitamin $B_5$ (pantothenic acid), vitamin $B_6$ (pyridoxal), folic acid, vitamin $B_{12}$ (cobalamin), biotin, etc. Vitamins B mainly function as coenzymes. Their functions include facilitating the oxidation of glucose and energy release from fats and proteins to maintain the normal functions of the nervous system. Vitamins are essential to the growth and regeneration of cells, the generation of erythrocyte, and the synthesis of nucleoprotein and myelin, and they can also activate the folic acid coenzyme to facilitate the generation of erythrocytes.

Vitamin E is considered an oxidation inhibitor, and it can inhibit platelet aggregation. Vitamin E can prevent the oxidation of erythrocyte membranes so as to protect the erythrocytes and prevent anemia. Vitamin E can also maintain the integrity of cell membrane so as to enhance the function of linolenic acid, protect the structure and function of muscles and nerve tissues, and increase the blood flow at capillaries to improve blood circulation. Although Vitamin E has the above-described activities, none of the commercially available products, such as those containing vitamin E and Wal Green or the vitamin E-containing L'oreal Furtur E, has the function of maintaining skin health and has the therapeutic efficacy for the acne, comedo, and zit, or can function as an anti-oxidant.

Activity assays show that a composition having the main components in ratios according to embodiments of the present invention shows excellent efficacy. It should be noted that although compositions according to the present invention comprise vitamin C, vitamin B complex, carotene, vitamin E, fragrance, thickening agents, and surfactants, the efficacy of these compositions cannot be predicted from ordinary skill in the art.

A composition in accordance with the invention mainly comprises 1-45% W/W vitamin C, 1-5% W/W vitamin B complex, 1-3% W/W carotene, 2-90% W/W vitamin E, 0.1-2% W/W fragrance, 1-5% W/W thickening agent, 1-8% W/W surfactant, and an appropriate amount of distilled water. The main components of the preferred composition may comprise 4-15% W/W vitamin C, 1-3% W/W vitamin B complex, 1-2% W/W carotene, and 20-65% W/W vitamin E.

This invention provides a Vitamin A acid-free composition. The composition is useful in the treatment of acne, comedo, zit by local application The composition comprises vitamin C, vitamin B complex, carotene, vitamin E, a fragrance, a thickening agent, and a surfactant, and, therefore, can be applied onto the local area of the body, such as the skin and face, to nourish skin, to treat and improve the symptoms of acne, comedo and zit, and to protect the skin from oxidation.

A topical composition of the present invention may include various excipients, carriers, or diluting agents known in the art, if needed, such that they can be formulated as an ointment, emulsion, lotion or patch that can be applied directly to the affected sites. Adhesives, such as starch, sodium carboxymethylcellulose, etc., may be added to those dosage forms using conventional techniques known in the art. Buffer salt such as phosphate may also be added to adjust the pH value to a proper range. Permeation enhancers or extracts from natural plants such as licorice root may also be added according to methods known in the art.

EXAMPLE 1

| Formulation | Lo-108 |
| --- | --- |
| Vitamin E | 65 |
| Vitamin C | 4 |
| Vitamin B complex | 1 |
| Carotene | 1 |
| Fragrance | 1 |
| Surfactant | 6.5 |
| Thickening agent | 4 |
| Distilled water | 30 |

In this formulation, vitamin C and vitamin B complex were dissolved in a small amount of distilled water, while carotene, vitamin E, a fragrance, a surfactant, and a thickening agent were mixed in a separate container. Then, these two were mixed, and a sufficient amount of distilled water was added therein to the required amount.

EXAMPLE 2

| Formulation | Lo-110 |
| --- | --- |
| Vitamin E | 20 |
| Vitamin C | 20 |
| Vitamin B complex | 2 |
| Carotene | 2 |
| Fragrance | 2 |
| Surfactant | 8 |
| Thickening agent | 1 |
| Distilled water | 20 |

In this formulation, vitamin C and vitamin B complex were dissolved in a small amount of distilled water, while carotene, vitamin E, a fragrance, a surfactant and a thickening agent were mixed in a separate container. Then, these two were mixed, and a sufficient amount of distilled water was added therein to the required amount.

EXAMPLE 3

| Formulation | Lo-122 |
| --- | --- |
| Vitamin E | 85 |
| Vitamin C | 2 |
| Vitamin B complex | 1 |
| Carotene | 1 |
| Fragrance | 0.1 |
| Surfactant | 3 |
| Thickening agent | 2 |
| Permeation enhancer | 0.5 |
| Distilled water | 15 |

In this formulation, vitamin C and vitamin B complex were dissolved in a small amount of distilled water, while carotene, vitamin E, a fragrance, a surfactant and a thickening agent were mixed in a separate container. Then, these two were mixed, and a sufficient amount of distilled water was added therein to the required amount.

EXAMPLE 4

| Formulation | Lo-130 |
| --- | --- |
| Vitamin E | 40 |
| Vitamin C | 10 |
| Vitamin B complex | 3 |
| Carotene | 2 |
| Fragrance | 2 |
| Surfactant | 10 |
| Thickening agent | 5 |
| Distilled water | 20 |

In this formulation, vitamin C and vitamin B complex were dissolved in a small amount of distilled water, while carotene, vitamin E, a fragrance, a surfactant, and a thickening agent were mixed in a separate container. Then, these two were mixed, and a sufficient amount of distilled water was added therein to the required amount.

EXAMPLE 5

| Formulation | Lo-18 |
| --- | --- |
| Vitamin E | 90 |
| Vitamin C | 1 |
| Vitamin B complex | 1 |
| Carotene | 1 |
| Fragrance | 0.5 |
| Surfactant | 3 |
| Thickening agent | 3 |
| Distilled water | qs |

In this formulation, vitamin C and vitamin B complex were dissolved in a small amount of distilled water, while carotene, vitamin E, a fragrance, a surfactant, and a thickening agent were mixed in a separate container. Then, these two were mixed, and a sufficient amount of distilled water was added therein to the required amount.

EXAMPLE 6

| Formulation | Lo-27 |
| --- | --- |
| Vitamin E | 30 |
| Vitamin C | 45 |
| Vitamin B complex | 1 |
| Carotene | 2 |
| Fragrance | 2 |

-continued

| Formulation | Lo-27 |
|---|---|
| Surfactant | 8 |
| Thickening agent | 1 |
| Permeation enhancer | 0.1 |
| Distilled water | qs |

In this formulation, vitamin C and vitamin B complex were dissolved in a small amount of distilled water, while carotene, vitamin E, a fragrance, a surfactant, and a thickening agent were mixed in a separate container. Then, these two were mixed, and a sufficient amount of distilled water was added therein to the required amount.

EXAMPLE 7

| Formulation | Lo-22 |
|---|---|
| Vitamin E | 80 |
| Vitamin C | 8 |
| Vitamin B complex | 4 |
| Carotene | 3 |
| Fragrance | 0.1 |
| Surfactant | 3 |
| Thickening agent | 2 |
| Distilled water | qs |

In this formulation, vitamin C and vitamin B complex were dissolved in a small amount of distilled water, while carotene, vitamin E, a fragrance, a surfactant, and a thickening agent were mixed in a separate container. Then, these two were mixed, and a sufficient amount of distilled water was added therein to the required amount.

EXAMPLE 8

| Formulation | Lo-39 |
|---|---|
| Vitamin E | 30 |
| Vitamin C | 10 |
| Vitamin B complex | 5 |
| Carotene | 2 |
| Fragrance | 2 |
| Surfactant | 10 |
| Thickening agent | 5 |
| Permeation enhancer | 1.5 |
| Distilled water | qs |

In this formulation, vitamin C and vitamin B complex were dissolved in a small amount distilled water, while carotene, vitamin E, a fragrance, a surfactant, and a thickening agent were mixed in a separate container. Then, these two were mixed, and a sufficient amount of distilled water was added therein to the required amount.

Activity Assays

Test 1: Lo-108 Therapeutic Efficacy Evaluation in Acne Patients

Material and method: An open clinical efficacy evaluation method is used in the study. Sixty patients, including 30 male and 30 female, were selected from outpatients suffering from acne during a six-month period from February to August 2001. The ages of these patients are between 17 and 42, with an average age of 25. Lo-108 was used over the six month period by local application to faces for 3 to 8 hours (overnight) each day. The patients returned to the clinic every other week to record the numbers of acnes and any property changes. The methods are as following:

1. The affected areas are washed and cleaned with facial wash (soap). After drying, the medication is applied to the affected areas.
2. The dosage is about 2 ml. The areas are then covered with gauze.
3. The medication is left on for at least three hours before it is washed off. No lotion (cream) should be used after washing.
4. If there are pustules, pus should be squeezed out before the medication is applied.

If patients have pustules, they are also given oral antibiotics, such as tetracycline or vibramycin, for a week. Other than that, they are prohibited from using other therapeutics for acne, such as oral or topical preparation of vitamin A acid or hormone therapy.

Based on the number of acnes, papules, and pustule, and the degree of the red swelling, the results were evaluated by the doctors and patients according to different grades and percent improvements.

TABLE 1

The results of therapy evaluation for Lo-108

| | Before Treatment (number) | After Treatment for 8 Weeks (number) |
|---|---|---|
| mean no. of comedoes | 43.5 | 20.1 ($p < 0.01$) |
| mean no. of papules | 21.0 | 2.1 ($p < 0.001$) |
| mean no. of pustules | 8.9 | 0 ($p < 0.0001$) |
| mean no. of cysts | 0.8 | 0 |

The results in table 1 show that after an 8-week treatment, the number of acne with black head or white head decreased significantly. The mean number changed from 43.5 to 20.1 ($p<0.01$). The mean number of red papules with constricted pore-opening reduced even more, from 21.0 to 2.1 ($p<0.001$). The pustules and the red-swelling cysts essentially disappeared, with the mean numbers changed, respectively, from 8.9 to 0, and from 0.8 to 0, leaving only erythemas or depressed scars. During the evaluation, Lo-108 was found to have anti-inflammatory, anti-fever, and anti-swelling effects. In addition, it can also inhibit hyperkeratosis of skin, thus making the skin smooth. Slight improvement in depressed scars only occurs with those having red swelling. This improvement probably results from detumescence.

The topical medicines for de-keratinization or topical antibiotics known in the art can cause many side effects, such as skin dryness, skin peeling, smarting, and even red swelling. However, these side effects did not occur after Lo-108 use due to its moisturizing function.

From the results listed above, Lo-108 is found to have therapeutic efficacy for acne. It also has the functions of de-keratinization, reducing sebum excretion, bacteria killing, anti-inflammation, and water retention in epidermis.

Test 2. Comparative Evaluation of the Inhibition of Sebum Excretion

Twenty healthy volunteers took part in this clinical trial and their ages range from 18 to 55. One side of the test subject's forehead skin was treated with Lo-108, and the side was left untreated as the control. The Lo-108 was administrated each night as follows: Lo-108 was applied to the skin with a dosage of 1 ml-2 ml. Then, it was washed off three hours later. The course of treatment was 4 weeks. The amounts of sebum on both sides of the forehead skin were determined each week at regular intervals.

Sebum excretion was determined as the amount of skin grease using the Sebometer 810 PC (Courage and Khazaka Ltd, Germany). By measuring percent differences of sebum excretion on both sides of the forehead skin, many interfering variables were minimized. The principle for determining sebum amount is as follows: An opaque plastic sheet of 0.1 mm thick and 64 mm$^2$ in size was pressed against the skin for 30 seconds. The transparency of the plastic sheet increases upon absorption of the sebum. There is a linear correlation between the transparency and the amount of sebum that has been absorbed. In other words, the amount of sebum is directly proportional to the transparency. As shown in table 2, data obtained from the photometer can be converted into mg/cm$^2$ using a formula.

TABLE 2

Determination Of Skin Grease

| Time | The mount of grease on the left and right sides of forehead skin (μg/cm$^2$) | |
| --- | --- | --- |
| | Test (Left Side) | Control (Right Side) |
| 0 week | 88.15 ± 58.21 | 93.85 ± 57.32 |
| 1 week | 82.80 ± 55.46 | 94 ± 60.45 |
| 2 week | 88.00 ± 42.60 | 112.55 ± 57.61 |
| 3 week | 81.75 ± 50.29 | 118.8 ± 57.61 |
| 4 week | 61.15 ± 37.37 | 99.95 ± 46.40 | with time (Pr>F 0.2854). The results listed above show that Lo-108 can effectively eliminate or suppress the excretion of grease for 12 hours or longer, and it can temporarily reduce sebum excretion at the sebaceous gland opening (the major cause of the acne). The efficacy of inhibiting sebum can be achieved in a short period of time and can be maintained for at least 4 weeks if the meditation is administered daily.

TABLE 3

The Amounts Of Sebum

| | Lo-108 Group | | Control group | |
| --- | --- | --- | --- | --- |
| Time (week) | Mean (μg/cm$^2$) | Standard deviation (SD) | Mean (μg/cm$^2$) | Standard deviation (SD) |
| 0 | 88.15 | 58.21 | 93.85 | 57.32 |
| 1 | 82.80 | 55.46 | 94.00 | 60.45 |
| 2 | 88.00 | 42.60 | 112.55 | 57.61 |
| 3 | 81.75 | 50.29 | 118.8 | 57.61 |
| 4 | 61.15 | 37.37 | 99.95 | 46.40 |

Note: Twenty patients participated in this test. The treatment group involves applying Lo-108 to the left sides of the foreheads; the control group involves applying the base ingredients without Lo-108 to the right sides of the foreheads.

TABLE 4

The Difference In Sebum Amounts

| Source | DF (Degree Of Freedom) | ANOVA SS | Mean Square | F Value | Pr > F (probability > F) |
| --- | --- | --- | --- | --- | --- |
| Patient Identification | 19 | 229013.20 | 12053.33 | 6.88 | 0.0001 |
| Treatment | 1 | 27518.58 | 27518.58 | 15.71 | 0.0001 |
| Number Of Treatments | 4 | 11278.55 | 2819.64 | 1.61 | 0.1740 |
| Treat * Time | 4 | 8869.17 | 2217.29 | 1.27 | 0.2854 |

Note:
Treat * Time represents the interactions between the treatments and time.

Because the test group and the control group were from the left and right sides of the same test subject's forehead skin, respectively, there is no need to take into account the variations in temperature, moisture, physical activities, and degrees of sweating of the volunteers. The amounts of grease on the foreheads in the test group are significantly lower than those of the control group based on statistical analysis using ANOVA (Analysis of variance). The difference is statistically significant (Pr>F 0.0001).

Referring to FIG. 1, the differences in weekly averages gradually become more apparent according to the ANOVA analysis. From the amounts of sebum excretion in the Lo-108 group shown in Table 3, the change in the sebum amount is statistically significant (pr>F 0.0001) after treatment for one week. From the results shown in Table 4, it is apparent that similar results are obtained if the medication is administered for a longer period of time, and the value does not increase Test 3. Burn And Wound Recovery In Animal Tests.

The average age of the male rats (Wistar strain) used in this experiment is 8 weeks. These animals are kept in the animal facility in Chenggong University, which is the only SPF qualified animal care facility in the southern Taiwan. The rats are kept in an animal room with air conditioning, and the temperature is maintained at 25±1° C. All animals are allowed to eat and drink freely.

Burn Experiment

The process of this experiment is performed according to the procedures of Kistler et al., and the same animals provide the self-controls. The experimental procedures are as follows:

Each rat is anesthetized with pentobarbital at a dosage of 65 mg/kg. After the rats go to deep slumber, the back of each rat is divided into four regions each having an area of about 4 cm$^2$. Hair in each region is shaved with a razor. Then, a red-hot iron sheet (about 80-85° C.) is put on the skin in the four regions for about 10 seconds to cause scalding on the back of the rats. After these processes, the iron sheets are removed and the wounds are sterilized and cleaned with hydrogen peroxide solution (37%). Then, the four regions are treated separately. While the control region is not treated with any medication, the other three regions are treated with vitamin E, the base of the test sample, and the test sample, respectively. The dosage used should be sufficient to cover the wound area. After treatment, the wounds are bandaged tightly to prevent bacterial infection. The bandages are changed and the wounds observed daily at the same time every day. Pictures of the wounds are taken at the same time daily. Seven days later, the rats are sacrificed, and the tissues from the four regions are removed for pathological section. Pathological changes of the wounds are evaluated by a pathology specialist in the Xinguang Medical Center.

Results

According to burn recovery, the regions treated with the product exhibit less inflammation. The results show that there is little difference between the control region and the region treated with the base of the product, while there is less inflammation in the regions treated with the products.

Wound Recovery Experiments

The average age of the male rats (Wistar strain) used in this experiment is also 8 weeks. According to the process described above, the back of the anesthetized rats is divided into four regions. The area of each region is about 4 cm$^2$, and rat hair in each region is removed with a razor. Then, an incision is made in each region of the back using a scalpel. The length of the incision is about 1 cm, and the incision should be deep enough to expose the muscle layer. Then, the wound is sterilized and cleaned with hydrogen peroxide solution (37%). Similar to the procedures described above, each region is treated with different treatments. The control region is not treated with any medication, and the other three regions are treated with vitamin E, the base ingredients of of the test sample, and the test sample, respectively. The dosage used should be sufficient to cover each region. After treatment, the wounds are bandaged tightly to prevent bacterial infection. The bandages are changed and the wounds observed daily at the same time every day. Pictures of the wounds are taken at the same time each day. Finally, the efficacy difference between the treatment groups is compared based on the days needed for the wound to recover. The fewer days needed, the faster the recovery.

Results

According to the wound recovery results, the wound treated with the product has a short recovery time, about 7.13±1.27 days (N=8). The recovery time in the control group is about 11.00±2.24 days (N=8). In the group treated with the base ingredients of the product, the recovery time is about 10.13±1.62 days (N=8). There is no significantly difference ($P>0.05$) between the control group and the group treated with the base ingredients of the product.

Test 4. Bacteriostasis Test

Three bacteria stains are used in this test: *Staphylococcus aureus*, Methicillin-resistant *Staphylococcus aureus* (ATCC33591), and *Propionibacterium acnes* (ATCC6919). Each of these bacteria is cultured separately in a proper medium, and tested with Lo-110 at 0.03 µl/ml, 0.1 µl/ml, 0.3 µl/ml, 1 µl/ml, 3 µl/ml, 10 µl/ml, 30 µl/ml and 100 µl/ml. The results show that the inhibitory concentration is 100 µl/ml.

Although the invention has been described in some detail by way of preferred embodiments, it will be obvious to those skilled in the art that certain modifications and changes may be practiced without departing from the scope of the invention.

What is claimed is:

1. A topical composition for transdermal administration, comprising:
    1-45% w/w vitamin C, 1-5% w/w vitamin B complex, 1-3% w/w carotene, and 2-90% w/w vitamin E, wherein the composition is substantially free of vitamin A or vitamin A acid.

2. The topical composition according to claim 1, comprising: 4-15% w/w vitamin C, 1-3% w/w vitamin B complex, 1-2% w/w carotene, and 20-65% w/w vitamin E.

3. The topical composition according to claim 1, further comprising 0.1-2% w/w fragrance, 1-5% w/w thickening agent, 1-8% w/w surfactant, and an appropriate amount of distilled water.

4. The topical composition according to claim 1, wherein the composition is for application to a local area of skin.

5. A topical composition for transdermal administration, said composition is for use in manufacturing a medication for treating acne, comedo or zit wherein the composition comprises: 1-45% w/w vitamin C, 1-5% w/w vitamin B complex, 1-3% w/w carotene, 2-90% w/w vitamin E, 0.1-2% w/w fragrance, 1-5% w/w thickening agent, 1-8% w/w surfactant, and an appropriate amount of distilled water, wherein the composition is substantially free of vitamin A or vitamin A acid.

6. A topical composition for transdermal administration, said composition is for skin-care, wherein the composition comprises: 1-45% w/w vitamin C, 1-5% w/w vitamin B complex, 1-3% w/w carotene, 2-90% w/w vitamin E, 0.1-2% w/w fragrance, 1-5% w/w thickening agent, 1-8% w/w surfactant, and an appropriate amount of distilled water, wherein the composition is substantially free of vitamin A or vitamin A acid.

7. A topical composition for transdermal administration, said composition has an antioxidant property, wherein the composition comprises: 1-45% w/w vitamin C, 1-5% w/w vitamin B complex, 1-3% w/w carotene, 2-90% w/w vitamin E, 0.1-2% w/w fragrance, 1-5% w/w thickening agent, 1-8% w/w surfactant, and an appropriate amount of distilled water, wherein the composition is substantially free of vitamin A or vitamin A acid.

8. A method for treating acne, comedo or zit, comprising applying a topical of claim 1 to skin of a subject in need thereof.

9. The topical composition according to claim 2, further comprising 0.1-2% w/w fragrance, 1-5% w/w thickening agent, 1-8% w/w surfactant, and an appropriate amount of distilled water.

* * * * *

UNITED STATES PATENT AND TRADEMARK OFFICE
CERTIFICATE OF CORRECTION

PATENT NO.      : 7,655,255 B2
APPLICATION NO. : 10/811420
DATED           : February 2, 2010
INVENTOR(S)     : Liu et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 622 days.

Signed and Sealed this

Twenty-third Day of November, 2010

David J. Kappos
*Director of the United States Patent and Trademark Office*